United States Patent

Takahashi et al.

[11] Patent Number: 5,488,509
[45] Date of Patent: Jan. 30, 1996

[54] LIGHT SOURCE APPARATUS FOR ENDOSCOPE

[75] Inventors: Tadashi Takahashi; Tetsuya Utsui; Rensuke Adachi; Mitsuru Iida; Katsuhiko Furuya; Junji Usami; Ryoji Honda, all of Tokyo, Japan

[73] Assignee: Asahi Kogaku Kogyo Kabushiki Kaisha, Tokyo, Japan

[21] Appl. No.: 281,083

[22] Filed: Jul. 27, 1994

[30] Foreign Application Priority Data

Aug. 19, 1993 [JP] Japan ............... 5-045135 U
Jun. 8, 1994 [JP] Japan ............... 6-125604

[51] Int. Cl.$^6$ ............... G02B 21/06; A61B 1/06
[52] U.S. Cl. ............... 359/385; 600/160
[58] Field of Search ............... 359/230, 234, 359/236, 384, 385, 379; 128/6; 358/98

[56] References Cited

U.S. PATENT DOCUMENTS

| | | | |
|---|---|---|---|
| 4,322,129 | 3/1982 | Takahashi et al. | 359/230 |
| 5,016,975 | 5/1991 | Sasaki et al. | 358/117 |
| 5,042,915 | 8/1991 | Akutsu et al. | 359/230 |
| 5,237,403 | 8/1993 | Sugimoto et al. | 128/6 |
| 5,277,172 | 1/1994 | Sugimoto | 359/230 |

FOREIGN PATENT DOCUMENTS

| | | |
|---|---|---|
| 61-41428 | 2/1986 | Japan. |
| 1200217 | 8/1989 | Japan. |

OTHER PUBLICATIONS

English language abstract of Japanese Publication No. 1-200217.

Primary Examiner—Paul M. Dzierzynski
Assistant Examiner—Steve Kong
Attorney, Agent, or Firm—Sandler, Greenblum & Bernstein

[57] ABSTRACT

A light source apparatus for an endoscope having a light source for emitting a bundle of illuminating light rays which are to be supplied to a light guide of the endoscope. The apparatus includes at least a pair of light-blocking plates disposed in the bundle of illuminating light rays to face each other across the optical axis of the ray bundle, and a device for supporting the light-blocking plates such that the plates are rotatable about an axis extending therebetween at right angles to the optical axis. At least one of the light-blocking plates has such a cross-sectional configuration as viewed in the optical axis direction that the light-blocking plate is bent at an angle to the axis of rotation near the center of the illuminating optical path.

22 Claims, 14 Drawing Sheets

LIGHT SOURCE APPARATUS FOR ENDOSCOPE

BACKGROUND OF THE INVENTION

1. Field of the Invention

The present invention relates to a light source apparatus for an endoscope which is designed so that it is possible to control the luminous flux of illuminating light that is supplied from a light source to the entrance end of a light guide.

2. Description of the Prior Art

A conventional endoscope light source apparatus of the type described above is generally arranged such that illuminating light emitted from a light source lamp is formed into a bundle of parallel rays by a reflecting mirror, and the parallel rays are focused by a condenser lens to enter the entrance end of an illuminating light guide.

In addition, a movable stop is provided in the intermediate portion of an illuminating optical path extending from the light source lamp to the entrance end of the light guide to control the luminous flux of illuminating light entering the light guide by blocking a desired cross-sectional area of the bundle of illuminating light rays from the outer edge thereof.

The conventional light source apparatus suffers, however, from the problem that the control of the incident luminous flux causes a change in the course of passage of illuminating light entering the light guide, resulting in considerable variation in the light-distribution and spectral characteristics of illuminating light emanating from the light guide. To overcome such a problem, it is necessary to use a complicated stop configuration and a complicated driving mechanism for the stop, which results in increase in the production cost.

To solve the above-described problems, Japanese Patent Application Laid-Open (KOKAI) No. 1-200217 proposes an arrangement in which at least a pair of light-blocking plates, which are formed in the shape of plane-parallel plates, are disposed between the condenser lens and the light source such that the light-blocking plates symmetrically face each other across the optical axis of the bundle of illuminating light rays, and in which the direction of the light-blocking plates is changed by rotating them about an axis which extends perpendicularly to the optical axis of the bundle of illuminating light rays and in parallel to the light-blocking plates, thereby controlling the luminous flux of illuminating light entering the light guide. With the proposed arrangement, it is possible to minimize variation in the light-distribution and spectral characteristics of illuminating light emanating from the light guide with a simple structure.

However, it is still impossible to avoid a change of the course of passage of illuminating light caused by a change in the luminous flux of illuminating light entering the light guide. Therefore, when the luminous flux of illuminating light entering the light guide is changed to a considerable extent, a distinct change occurs in the light-distribution and spectral characteristics of light emanating from the light guide, giving rise to a problem in practical use.

When a xenon lamp, which is bright and generates a relatively small quantity of heat, is used as a light source lamp, flicker is likely to occur in the central portion of the bundle of light rays emitted from the lamp because of an electric discharge between the electrodes or the convection of the xenon gas.

Such flicker is not so conspicuous in view of the whole illuminating light. However, as the cross-sectional area of the bundle of illuminating light rays is blocked from the marginal portion thereof, the proportion of central rays to the marginal rays increases and hence flicker becomes even more conspicuous, hindering to the endoscopic observation.

SUMMARY OF THE INVENTION

An object of the present invention is to provide a light source apparatus for an endoscope which has minimal variation in light-distribution and spectral characteristics even when the luminous flux of illuminating light entering a light guide of the endoscope is changed to a considerable extent, and which is simple in structure and capable of being produced at reduced cost.

Another object of the present invention is to provide a light source apparatus for an endoscope which is designed so that no conspicuous flicker occurs even when the illuminating optical path is partly blocked to control the luminous flux of illuminating light entering a light guide of the endoscope.

Other objects and advantages of the present invention will become apparent from the following detailed description of illustrated embodiments of the invention.

According to the present invention, there is provided a light source apparatus for an endoscope having a light source for emitting a bundle of illuminating light rays which are to be supplied to a light guide of the endoscope. The light source apparatus includes at least a pair of light-blocking plates disposed in the bundle of illuminating light rays to face each other across the optical axis of the bundle of illuminating light rays, and a device for supporting the light-blocking plates in such a manner that the light-blocking plates are rotatable about an axis extending between the light-blocking plates at right angles to the optical axis of the bundle of illuminating light rays. At least one of the light-blocking plates has such a cross-sectional configuration as viewed in the direction of the optical axis of the bundle of illuminating light rays when the surfaces of the light-blocking plates lie parallel to the optical axis that the light-blocking plate is bent at an angle to the axis of rotation at a position near the center of the illuminating optical path.

In addition, there is provided a light source apparatus for an endoscope having a light source for emitting a bundle of illuminating light rays which are to be supplied to a light guide of the endoscope. The light source apparatus includes at least a pair of light-blocking plates disposed in parallel in the bundle of illuminating light rays to face each other across the optical axis of the bundle of illuminating light rays. The light-blocking plates are plane-parallel plates. The light source apparatus further includes a device for supporting the light-blocking plates in such a manner that the light-blocking plates are rotatable about an axis which is parallel to the surfaces of the light-blocking plates and perpendicular to the optical axis of the bundle of illuminating light rays. The light-blocking plates are disposed such that the distances from these light-blocking plates to the axis of rotation are different from each other.

In addition, there is provided a light source apparatus for an endoscope having a light source for emitting a bundle of illuminating light rays which are to be supplied to a light guide of the endoscope. The light source apparatus includes at least a pair of light-blocking plates disposed in parallel in the bundle of illuminating light rays to face each other across the optical axis of the bundle of illuminating light rays. The light-blocking plates are different in length in the direction of the optical axis. The light source apparatus further includes a device for supporting the light-blocking plates in such a manner that the light-blocking plates are rotatable about an axis which is perpendicular to the optical axis of the bundle of illuminating light rays and extends between the light-blocking plates.

In addition, there is provided a light source apparatus for an endoscope having a light source for emitting a bundle of illuminating light rays which are to be supplied to a light guide of the endoscope. The light source apparatus includes at least a pair of light-blocking plates disposed in parallel in the bundle of illuminating light rays to face each other across the optical axis of the bundle of illuminating light rays, and a device for supporting the light-blocking plates in such a manner that the light-blocking plates are rotatable about an axis extending between the light-blocking plates at right angles to the optical axis of the bundle of illuminating light rays. The light source apparatus further includes a central light-blocking plate for blocking the central portion of the bundle of illuminating light rays as the bundle of illuminating light rays is gradually blocked by the light-blocking plates as rotated.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
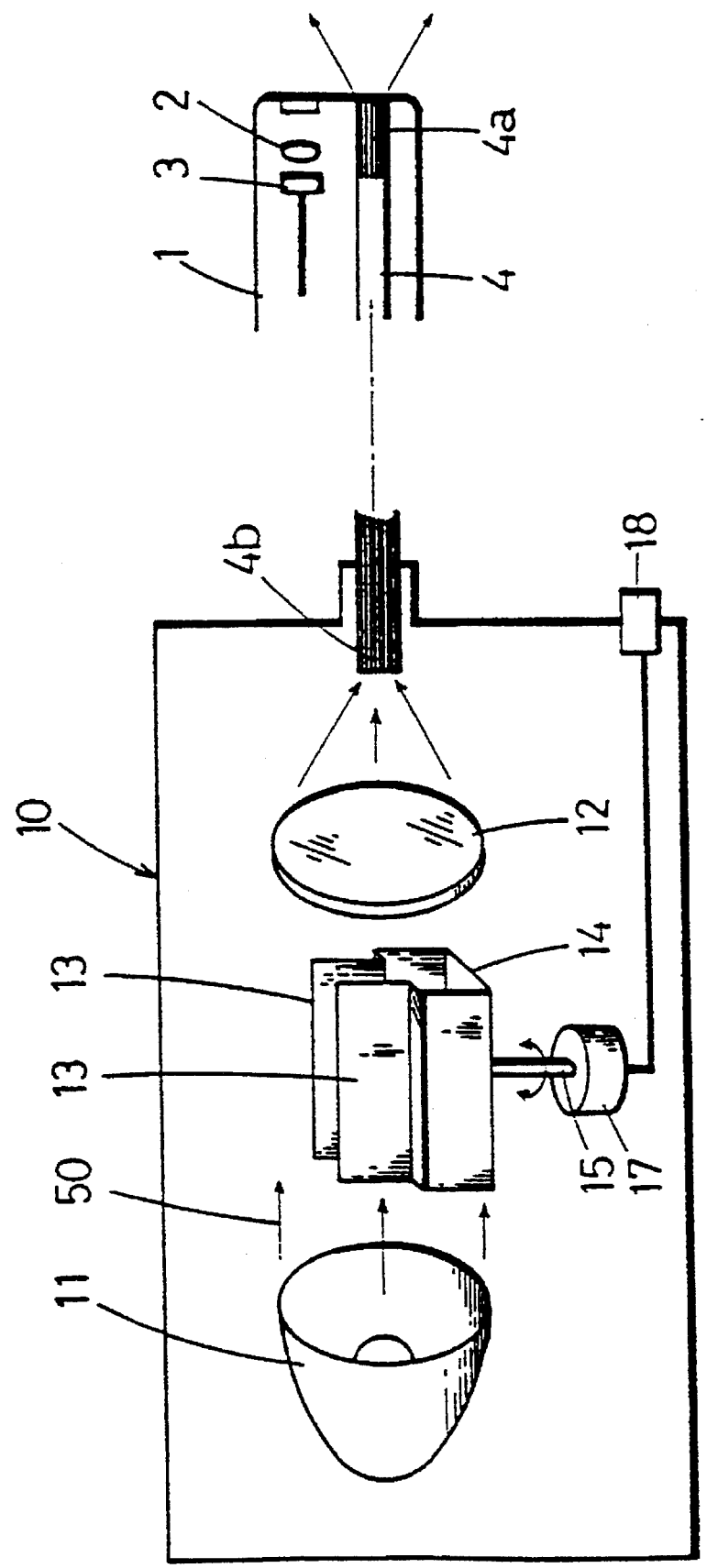
FIG. 1 is a schematic view showing the whole of a first embodiment of the present invention.

Referring to FIG. 1, which schematically shows a first embodiment of the present invention, an insert part 1 of an endoscope has an objective lens 2 disposed in the distal end portion thereof. A solid-state imaging device 3 is disposed such that a light-receiving surface thereof lies at a position where an image of an object is formed by the objective lens 2. It should be noted that an image guide fiber bundle may be used in place of the solid-state imaging device 3.

An illuminating light guide fiber bundle 4 is used to illuminate the visual field of the objective lens 2. More specifically, a part which is under observation is illuminated with illuminating light emanating from the exit end 4a of the light guide fiber bundle 4.

A light source apparatus 10 supplies illuminating light to the light guide fiber bundle 4. The entrance end 4b of the light guide fiber bundle 4 is removably inserted into the light source apparatus 10.

Illuminating light is emitted in the form of a bundle of parallel rays from a light source lamp 11 which is disposed in the light source apparatus 10. The illuminating light is then converged by a condenser lens 12 to enter the entrance end 4b of the light guide fiber bundle 4. As the light source lamp 11, for example, a halogen lamp or a xenon lamp may be used.

A pair of thin and opaque light-blocking plates 13 are provided in an illuminating optical path between the light source lamp 11 and the condenser lens 12 to block a part or the whole of a bundle of parallel illuminating light rays 50 before it reaches the condenser lens 12. The light-blocking plates 13 are disposed in parallel to face each other across the optical axis of the bundle of illuminating light rays 50. The pair of light-blocking plates 13 are formed to be equal to each other in dimensions such as the height and the length in the direction of the optical axis. Since the light-blocking plates 13 are thin, when they are disposed with their surfaces lying parallel to the optical axis of the bundle of illuminating light rays 50, as shown in FIG. 1, substantially no part of the bundle of illuminating light rays 50 is blocked.

Figure 2:
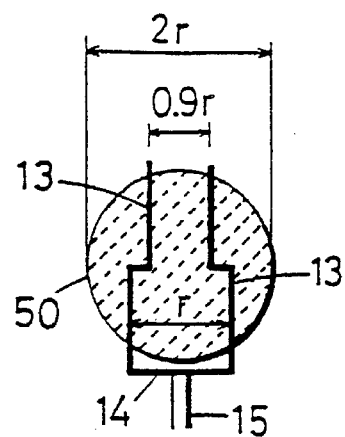
FIG. 2 is a front view of light-blocking plates in the first embodiment of the present invention.

FIG. 2 shows cross-sections of the pair of light-blocking plates 13 as viewed in the optical axis direction of the bundle of illuminating light rays 50 when the plate surfaces lie parallel to the optical axis. As is clear from the figure, each light-blocking plate 13 has such a crank-shaped cross-sectional configuration that the light-blocking plate 13 is bent at right angles twice at a position near the center of the bundle of illuminating light rays 50.

The pair of light-blocking plates 13 are connected at their bottoms by a connecting plate 14 and thus integrated into one unit. A rotating shaft 15 is rigidly secured to the center of the bottom of the connecting plate 14 such that the rotating shaft 15 is perpendicular to the optical axis of the bundle of illuminating light rays 50 and parallel to the light-blocking plates 13. By rotating the rotating shaft 15 with a motor 17 such as a step motor or by hand, the light-blocking plates 13 can be rotated about an axis containing the rotating shaft 15 and stopped at a desired position.

The rotation of the light-blocking plates 13 causes a change in the cross-sectional area of the bundle of illuminating light rays 50, resulting in a change in the luminous flux of illuminating light entering the light guide fiber bundle 4. Reference numeral denotes a switch 18 which is actuated to control the operation of the motor 17.

FIG. 2 shows the pair of light-blocking plates 13 as viewed in the optical axis direction of the bundle of illuminating light rays 50 when the plate surfaces lie parallel to the optical axis. As viewed in this direction, the light-blocking plates 13 are in bilateral symmetry with respect to the rotating shaft 15. Assuming that the effective radius of the bundle of illuminating light rays 50 at this part is r, the distance between the two light-blocking plates 13 is r at the lower halves thereof and 0.9r at the upper halves thereof.

Figure 3:
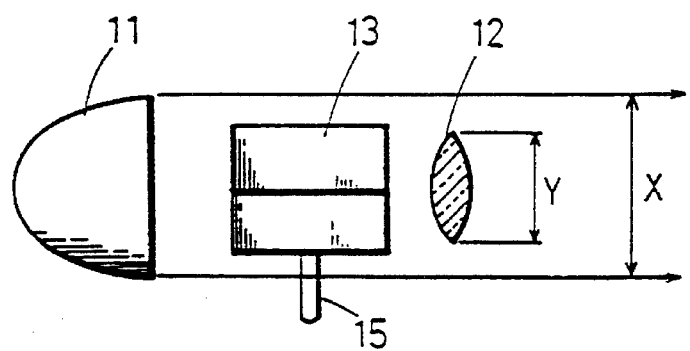
FIG. 3 is a side view of an illuminating optical path in the first embodiment of the present invention.

However, when, as shown in FIG. 3, the diameter X of the bundle of illuminating light rays 50 emitted from the light source lamp 11 is larger than the diameter Y of the condenser lens 12, the diameter Y of the condenser lens 12 is the effective diameter (i.e., the effective radius r=Y/2); when X is not larger than Y, r=X/2.

The relationship between the distance between the light-blocking plates 13 and the length thereof in the optical axis direction has a large effect on the relationship between the angle of rotation of the light-blocking plates 13 and the luminous flux of illuminating light entering the light guide fiber bundle 4. Therefore, the dimensions are determined by taking the surrounding space into consideration. In this embodiment, the length of each light-blocking plate 13 in the optical axis direction is set at 2r.

Figure 4:
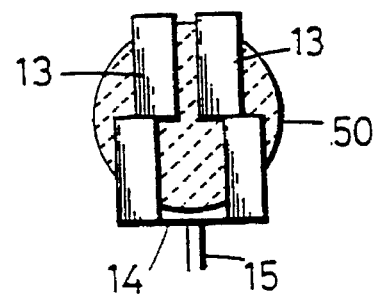
FIG. 4 is a front view of the light-blocking plates in the first embodiment in a state where they have been rotated to a certain extent.

FIG. 4 shows the light-blocking plates 13 in a state where they have been rotated to a certain extent about the rotating shaft 15 to block a part of the effective bundle 50 of illuminating light rays. The larger the cross-sectional area blocked by the light-blocking plates 13, the smaller the luminous flux of illuminating light entering the light guide fiber bundle 4.

Figure 5:
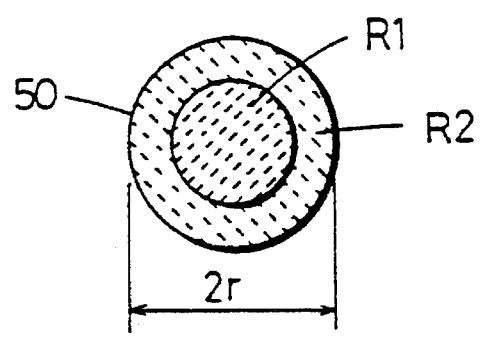
FIG. 5 is a front view of a bundle of illuminating light rays in the first embodiment of the present invention.

As shown in FIG. 5, the effective bundle 50 of illuminating light rays is divided into a central ray bundle R1 and a marginal ray bundle R2. In this case, the central ray bundle R1 and the marginal ray bundle R2 are divided so that in a totally-open state where the effective ray bundle 50 is not blocked by the light-blocking plates 13, the luminous flux of the central ray bundle R1 and that of marginal ray bundle R2 are equal to each other.

If the ratio of the marginal ray bundle R2 to the central ray bundle R1 does not substantially change as the light-blocking plates 13 are rotated, the variation in the light-distribution and spectral characteristics of illuminating light emanating from the light guide fiber bundle 4 toward the part under observation is small.

Figure 6:
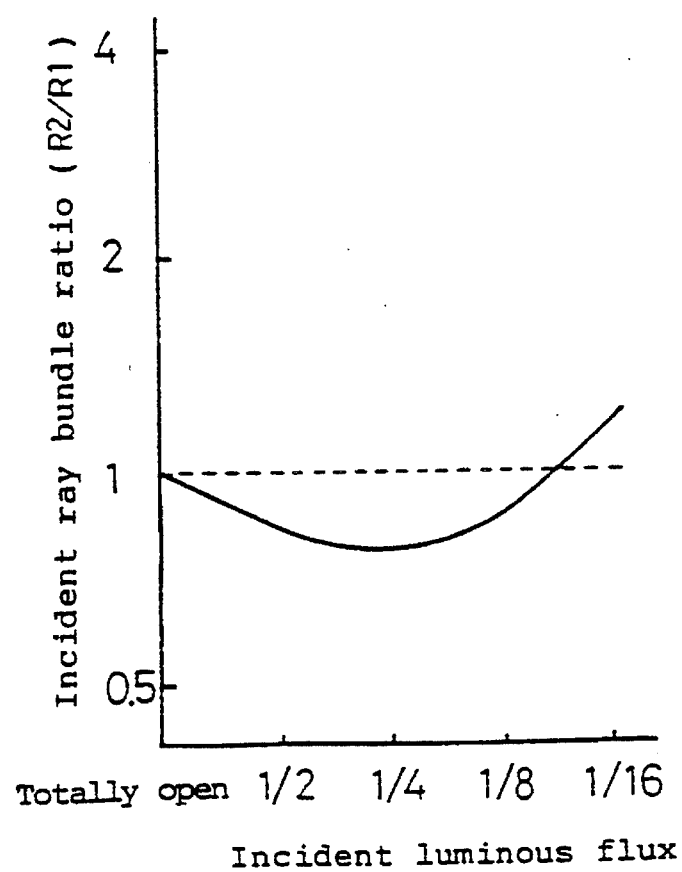
FIG. 6 is a graph showing luminous flux characteristics of illuminating light in the first embodiment of the present invention.

FIG. 6 shows the relationship between the luminous flux of illuminating light entering the light guide fiber bundle 4, which decreases as the light-blocking plates 13 are rotated about the rotating shaft 15, and the ratio of the marginal ray bundle R2 to the central ray bundle R1 in the above-described first embodiment.

As will be clear from the graph of FIG. 6, the change in the ratio of the marginal ray bundle R2 to the central ray bundle R1 is satisfactorily small over the entire range of from the totally-open position where the luminous flux incident on the light guide fiber bundle 4 is not cut off to the position where it is reduced to $\frac{1}{16}$. Consequently, it is possible to minimize the variation in the light-distribution and spectral characteristics of illuminating light emanating from the light guide fiber bundle 4.

Figure 7:
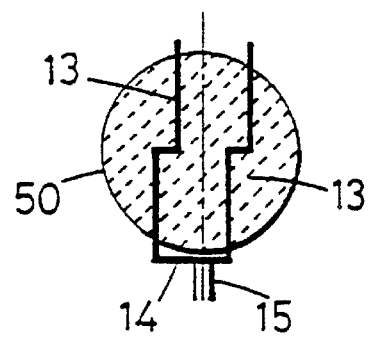
FIG. 7 is a front view of light-blocking plates in a second embodiment of the present invention.

FIG. 7 shows a pair of light-blocking plates 13 in a second embodiment of the present invention. The figure shows cross-sections of the pair of light-blocking plates 13 as viewed in the optical axis direction. As will be clear from the figure, the light-blocking plates 13 have crank-shaped cross-sectional configurations which are not in bilateral symmetry but in point symmetry with respect to the optical axis of the bundle of illuminating light rays 50. In this case also, the same advantages as those in the first embodiment can be obtained.

Figure 8:
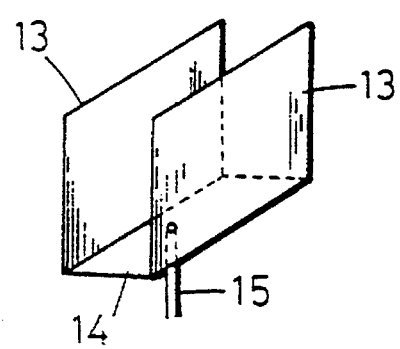
FIG. 8 is a perspective view of light-blocking plates in a third embodiment of the present invention.
Figure 9:
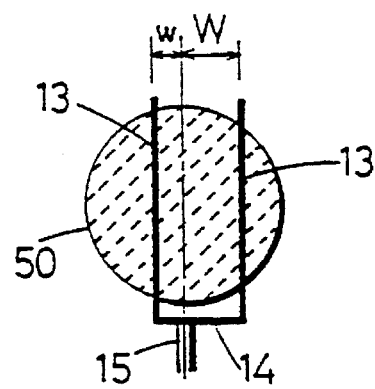
FIG. 9 is a front view of the light-blocking plates in the third embodiment of the present invention.
Figure 10:
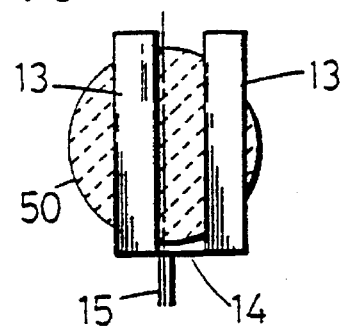
FIG. 10 is a front view of the light-blocking plates in the third embodiment in a state where they have been rotated to a certain extent.

FIGS. 8 to 10 show light-blocking plates 13 in a third embodiment of the present invention. The light-blocking plates 13 are formed in the shape of plane-parallel plates. The light-blocking plates 13 are disposed such that the distances from these light-blocking plates 13 to the rotating shaft 15 are different from each other (w<W). FIGS. 8 and 9 are perspective and front views of the light-blocking plates 13. FIG. 10 is a front view of the light-blocking plates 13 in a state where they have been rotated to a certain extent.

In the third embodiment also, it is possible to obtain advantages approximately similar to those in the first and second embodiments by virtue of the symmetry of the ray bundle. Thus, it is possible to minimize the variation in the light-distribution and spectral characteristics of illuminating light over the entire range from the totally-open position to the 1/16 position.

Figure 11:
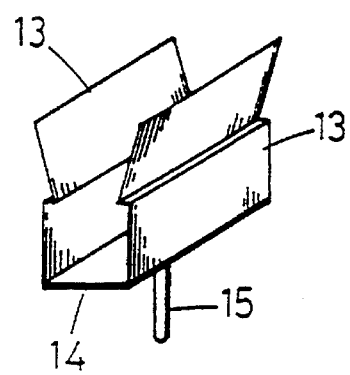
FIG. 11 is a perspective view of light-blocking plates in a fourth embodiment of the present invention.
Figure 12:
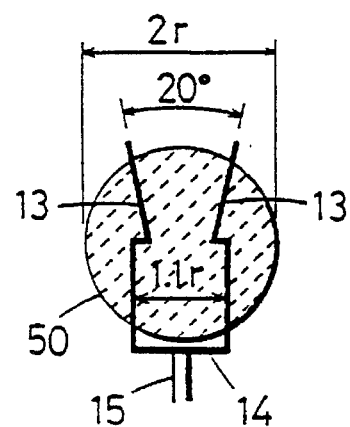
FIG. 12 is a front view of the light-blocking plates in the fourth embodiment of the present invention.
Figure 13:
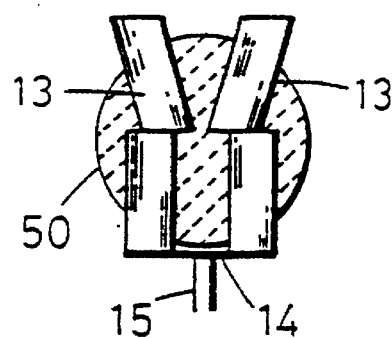
FIG. 13 is a front view of the light-blocking plates in the fourth embodiment in a state where they have been rotated to a certain extent.

FIGS. 11 to 13 show light-blocking plates 13 in a fourth embodiment of the present invention. At their lower halves, the pair of light-blocking plates 13 extend in parallel to face each other across the rotating shaft 15 at an equal distance of 0.55r from the rotating shaft 15. Each light-blocking plate 13 is bent at an intermediate portion thereof to slightly extend inwardly and then bent at the inward end to extend upwardly away from the axis of the rotating shaft 15 at an angle of 10 degrees to it. FIGS. 11 and 12 are perspective and front views of the light-blocking plates 13. FIG. 13 is a front view of the light-blocking plates 13 in a state where they have been rotated to a certain extent.

Figure 14:
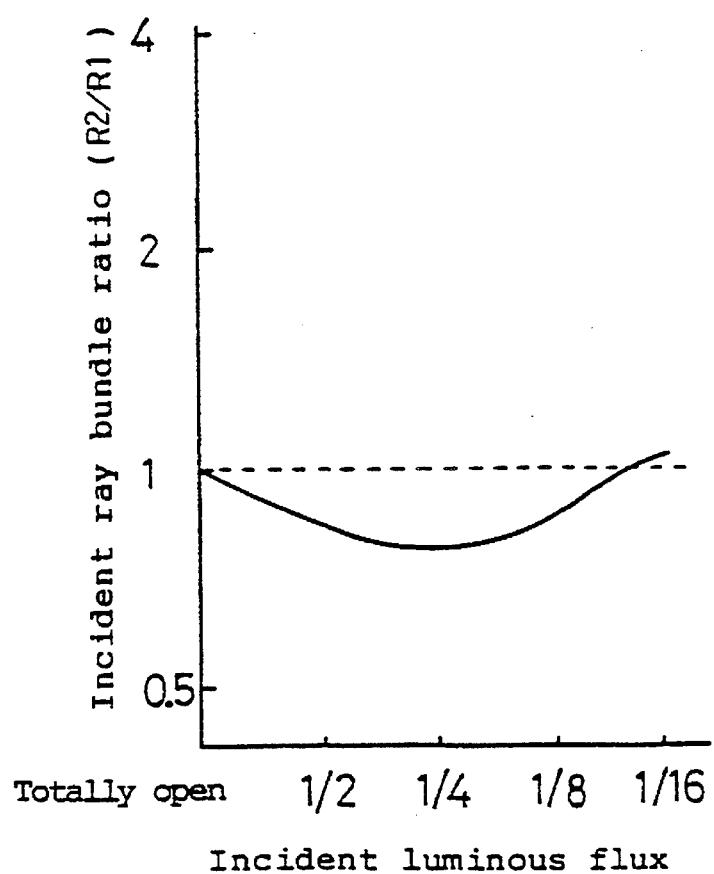
FIG. 14 is a graph showing luminous flux characteristics of illuminating light in the fourth embodiment of the present invention.

FIG. 14 shows the relationship between the luminous flux of illuminating light entering the light guide fiber bundle 4 and the ratio of the marginal ray bundle R2 to the central ray bundle R1 in the above-described fourth embodiment.

As will be clear from the graph of FIG. 14, the change in the ratio of the marginal ray bundle R2 to the central ray bundle R1 is also satisfactorily small over the entire range from the totally-open position, where the luminous flux incident on the light guide fiber bundle 4 is not cut off, to the position where it is reduced to 1/16.

Figure 15:
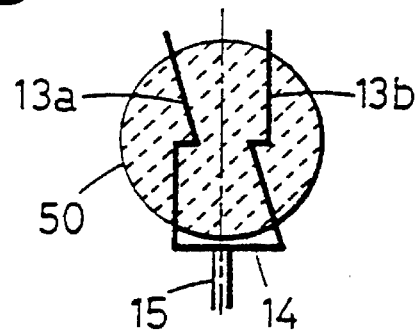
FIG. 15 is a front view of light-blocking plates in a fifth embodiment of the present invention.

FIG. 15 is a front view of light-blocking plates 13a and 13b in a fifth embodiment of the present invention. One light-blocking plate 13a has the same configuration as that of each light-blocking plate 13 in the fourth embodiment, whereas the other light-blocking plate 13b is in point symmetry with the light-blocking plate 13a with respect to the optical axis of the bundle of illuminating light rays 50. In this embodiment also, advantages approximately similar to those in the fourth embodiment can be obtained.

Figure 16:
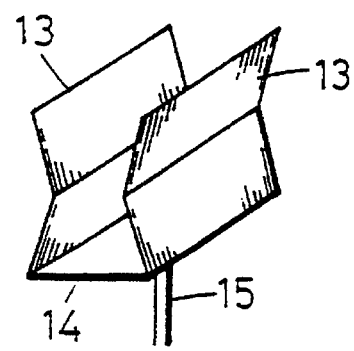
FIG. 16 is a perspective view of light-blocking plates in a sixth embodiment of the present invention.
Figure 17:
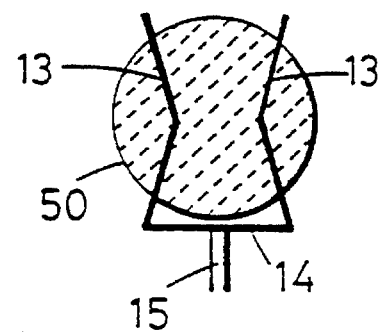
FIG. 17 is a front view of the light-blocking plates in the sixth embodiment of the present invention.
Figure 18:
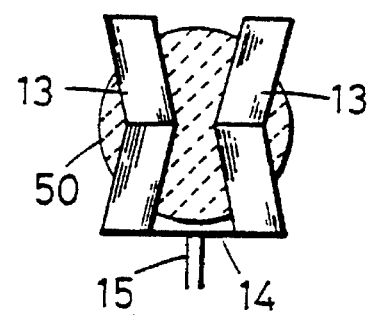
FIG. 18 is a front view of the light-blocking plates in the sixth embodiment in a state where they have been rotated to a certain extent.

FIGS. 16 to 18 show light-blocking plates 13 in a sixth embodiment of the present invention. The pair of light-blocking plates 13 are each bent in the shape of an angular bracket as viewed in the optical axis direction so that the upper halves of the light-blocking plates 13 extend upwardly away from each other, and the lower halves thereof extend downwardly away from each other. Thus, the two light-blocking plates 13 define a configuration in which the spacing between the light-blocking plates 13 reaches a minimum at the intermediate portions thereof.

Figure 19:
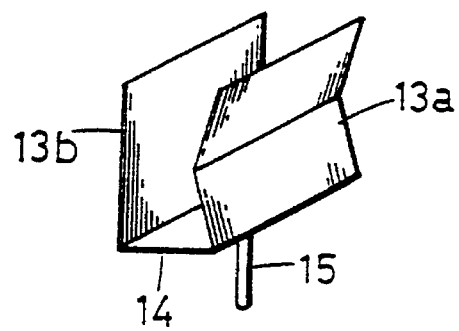
FIG. 19 is a perspective view of light-blocking plates in a seventh embodiment of the present invention.
Figure 20:
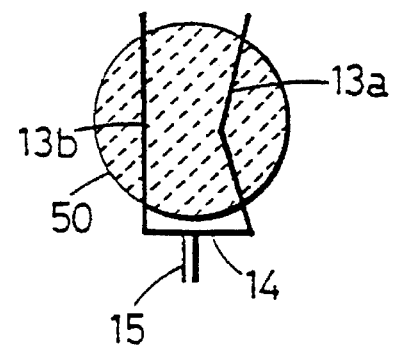
FIG. 20 is a front view of the light-blocking plates in the seventh embodiment of the present invention.
Figure 21:
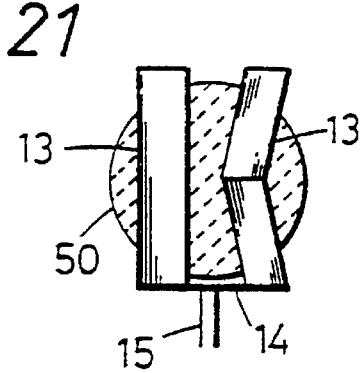
FIG. 21 is a front view of the light-blocking plates in the seventh embodiment in a state where they have been rotated to a certain extent.

FIGS. 19 to 21 show light-blocking plates 13a and 13b in a seventh embodiment of the present invention. Of the pair of light-blocking plates 13a and 13b, one light-blocking plate 13a is bent in the same way as in the sixth embodiment, while the other light-blocking plate 13b is formed in the shape of a flat plate.

Figure 22:
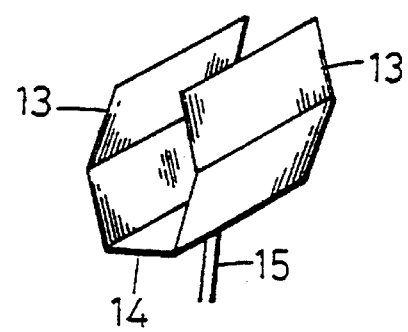
FIG. 22 is a perspective view of light-blocking plates in an eighth embodiment of the present invention.
Figure 23:
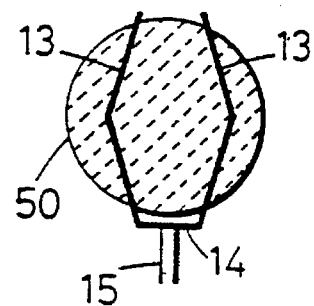
FIG. 23 is a front view of the Night-blocking plates in the eighth embodiment of the present invention.
Figure 24:
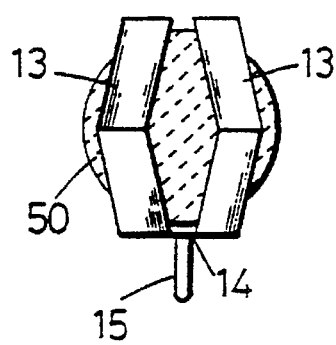
FIG. 24 is a front view of the light-blocking plates in the eighth embodiment in a state where they have been rotated to a certain extent.

FIGS. 22 to 24 show light-blocking plates 13 in an eighth embodiment of the present invention. In contrast to the light-blocking plates 13 in the sixth embodiment, the light-blocking plates 13 in this embodiment are disposed so that the upper halves of the light-blocking plates 13 extend upwardly toward each other, and the lower halves thereof extend downwardly toward each other. Thus, the light-blocking plates 13 define a configuration in which the spacing between the light-blocking plates 13 reaches a maximum at the intermediate portions thereof.

In the sixth to eighth embodiments also, it is possible to obtain advantages similar to those in the fourth embodiment, which is shown in FIGS. 11 to 13. However, the sixth embodiment, shown in FIGS. 16 to 18, is particularly effective in a case where the length of the light-blocking plates 13 in the optical axis direction is relatively long, whereas the eighth embodiment, shown in FIGS. 22 to 24, is particularly effective in a case where the length of the light-blocking plates 13 in the optical axis direction is relatively short.

Figure 25:
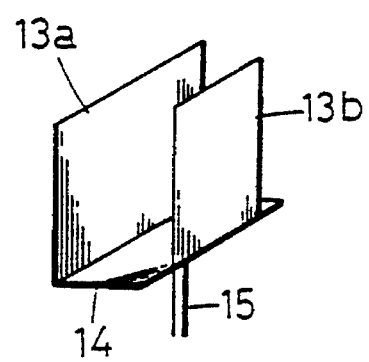
FIG. 25 is a perspective view of light-blocking plates in a ninth embodiment of the present invention.
Figure 26:
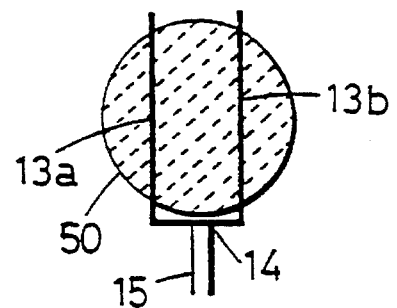
FIG. 26 is a front view of the light-blocking plates in the ninth embodiment of the present invention.
Figure 27:
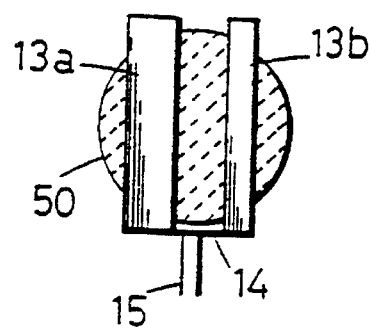
FIG. 27 is a front view of the light-blocking plates in the ninth embodiment in a state where they have been rotated to a certain extent.

FIGS. 25 to 27 show light-blocking plates 13a and 13b in a ninth embodiment of the present invention. The pair of light-blocking plates 13a and 13b are formed in the shape of plane-parallel plates such that the length of one light-blocking plate 13a in the optical axis direction is longer than that of the other light-blocking plate 13b.

With the above-described arrangement, a change in the ratio of the marginal ray bundle R2 to the central ray bundle R1, which occurs as the luminous flux incident on the light guide fiber bundle 4 is reduced, can be made small in comparison to a case where a pair of plane-parallel plates of the same size are combined together.

Figure 28:
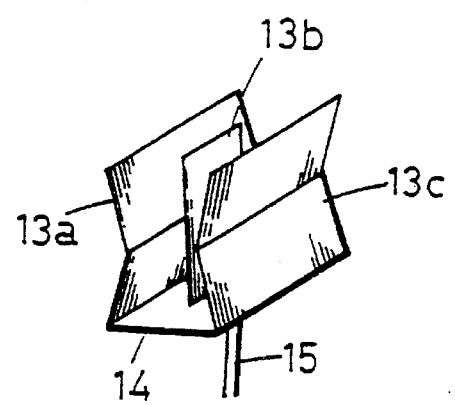
FIG. 28 is a perspective view of light-blocking plates in a tenth embodiment of the present invention.
Figure 29:
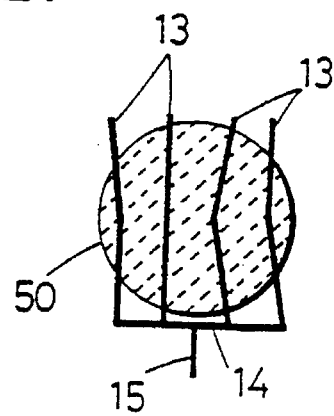
FIG. 29 is a front view of light-blocking plates in an eleventh embodiment of the present invention.

Although in the foregoing embodiments a pair of light-blocking plates are provided, it should be noted that the present invention is not necessarily limited thereto. For example, three light-blocking plates 13a, 13b and 13c (i.e., a pair of light-blocking plates plus one) may be provided as in the case of a tenth embodiment (FIG. 28) of the present invention. In this case, the length of the central light-blocking plate 13b in the optical axis direction should preferably be made shorter than those of the left and right (as viewed in FIG. 28) light-blocking plates 13a and 13c. It is also possible to provide four (two pairs of) light-blocking plates 13 as in the case of an eleventh embodiment (shown in FIG. 29) of the present invention. It is also possible to provide five or more light-blocking plates 13.

Figure 30:
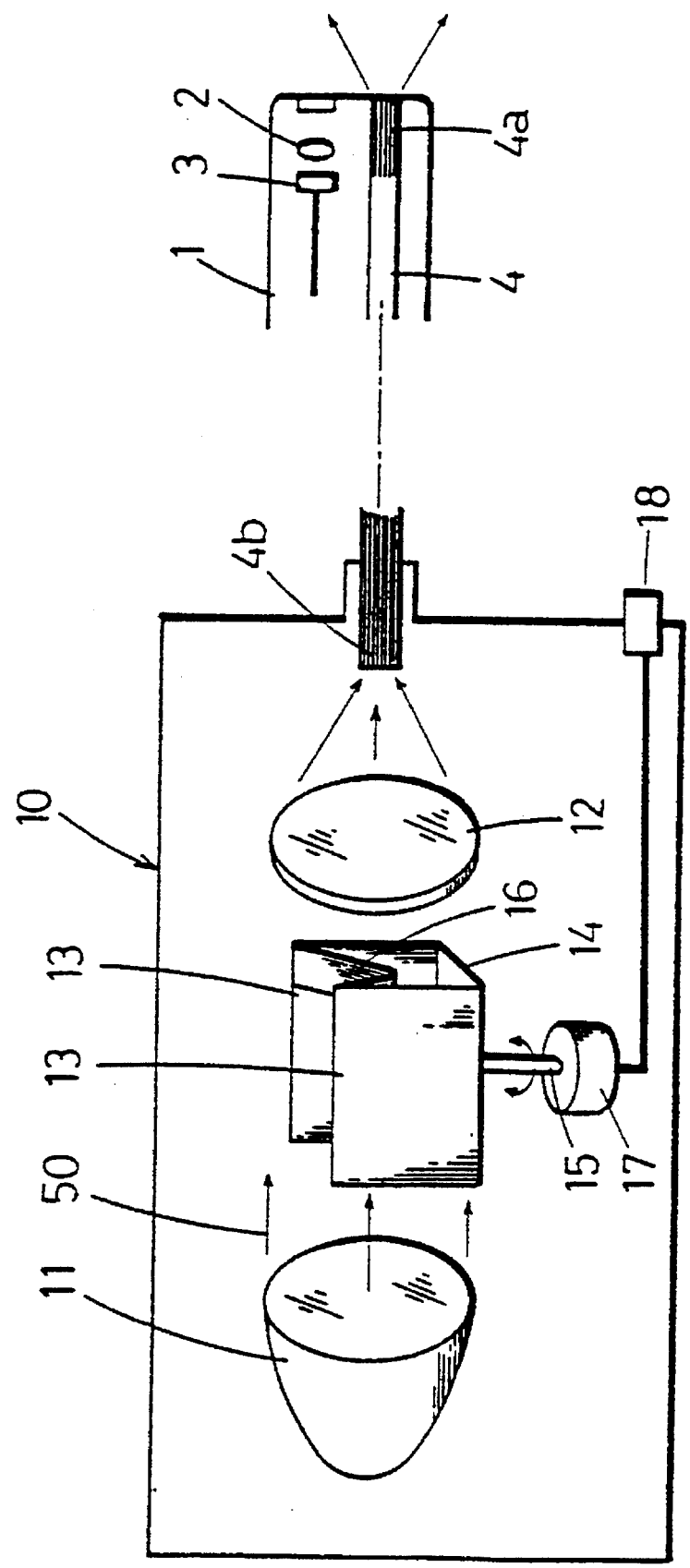
FIG. 30 is a schematic view showing the whole of a twelfth embodiment of the present invention.

FIG. 30 shows a twelfth embodiment of the present invention. The arrangement of this embodiment is the same as that of the first embodiment except for the light-blocking plates 13. In the twelfth embodiment, however, a xenon lamp is used as the light source lamp 11.

The pair of light-blocking plates 13 are formed in the shape of rectangular plane-parallel plates of the same size. The light-blocking plates 13 are connected together by a connecting plate 14 to define a U-shaped cross-sectional configuration as a whole.

A pair of central light-blocking plates 16, which are made of the same thin metallic plates as the light-blocking plates 13, extend obliquely downward from the respective upper ends of the forward end portions of the light-blocking plates 13 toward the center of the bundle of illuminating light rays 50. Thus, only at this portion, the U-shaped opening of the light-blocking plate assembly has an M-shaped cross-sectional configuration.

Figure 31:
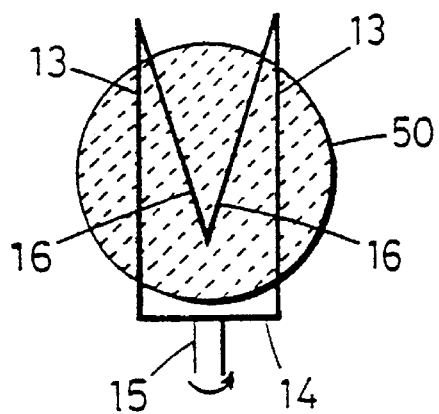
FIG. 31 is a front view of light-blocking plates in the twelfth embodiment of the present invention.

FIGS. 31 to 34 are front views of the illuminating optical path where the light-blocking plates 13 and the central light-blocking plates 16 are disposed together as one unit. FIG. 31 shows a state where the surfaces of the light-blocking plates 13 and 16 are placed parallel to the optical axis of the bundle of illuminating light rays 50 so that none of the light-blocking plates 13 and 16 block the bundle of illuminating light rays 50.

As the light-blocking plates 13 and 16 which are in the state as shown in FIG. 31 are gradually rotated about the rotating shaft 15, the left and right halves of the bundle of illuminating light rays 50 are gradually blocked by the light-blocking plates 13 in such a manner that the blocked areas of the left and right halves of the ray bundle 50 are equal and become wider.

Figure 32:
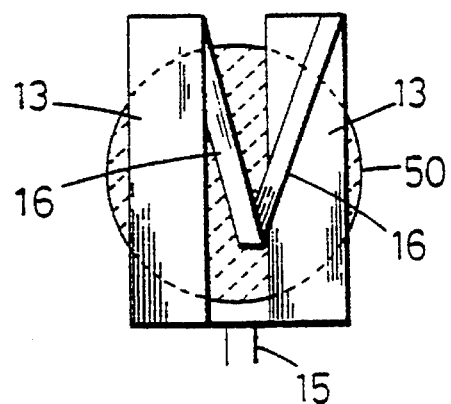
FIG. 32 is a front view of the light-blocking plates in the twelfth embodiment in a state where they have been slightly rotated.
Figure 33:
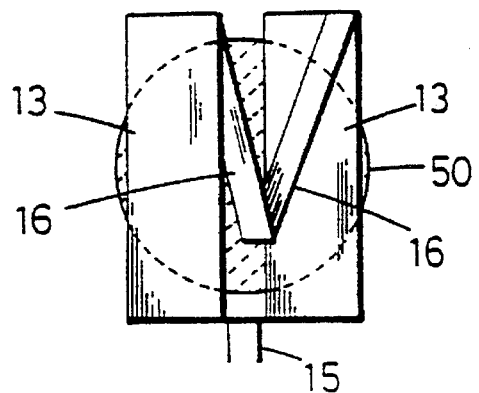
FIG. 33 is a front view of the light-blocking plates in the twelfth embodiment in a state where they have been further rotated.
Figure 34:
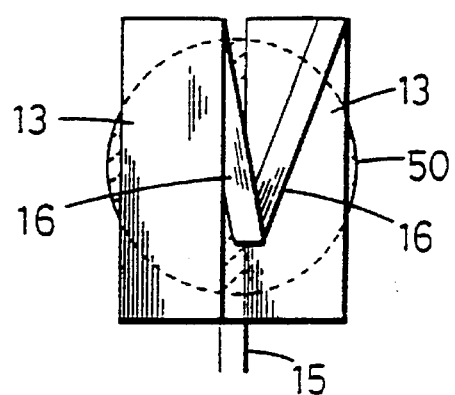
FIG. 34 is a front view of the light-blocking plates in the twelfth embodiment in a state where they have been still further rotated.

As shown in FIGS. 32 to 34, the central portion of the bundle of illuminating light rays 50 is increasingly blocked by the central light-blocking plates 16 as the light-blocking plates 13 and 16 are rotated. Accordingly, even when the light-blocking area is widened to reduce the luminous flux of illuminating light entering the light guide fiber bundle 4, there is no increase in the proportion of light in the central portion of the bundle of illuminating light rays 50 to the bundle of incident light rays. Therefore, flicker of illuminating light is inconspicuous.

It should be noted that the width and length of the central light-blocking plates 16 and the installation position thereof with respect to the light-blocking plates 13 may be appropriately selected according to design conditions. The central light-blocking plates 16 may be provided at any position on the light-blocking plates 13.

Figure 35:
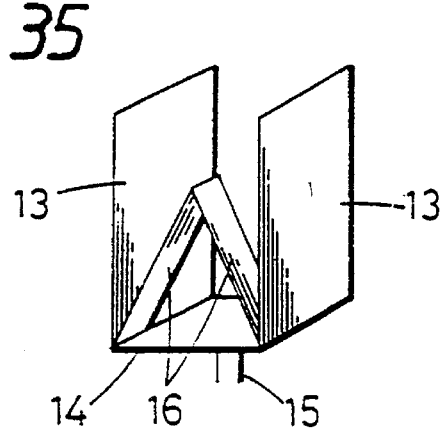
FIG. 35 is a perspective view of light-blocking plates in a thirteenth embodiment of the present invention.
Figure 36:
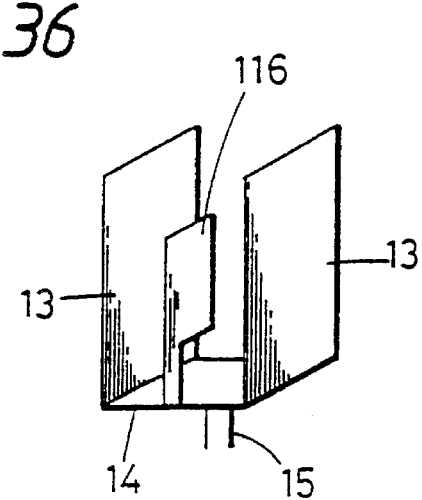
FIG. 36 is a perspective view of light-blocking plates in a fourteenth embodiment of the present invention.

As shown in FIG. 35, which illustrates a thirteenth embodiment of the present invention, the central light-blocking plates 16 may be disposed to extend upwardly from the connecting plate 14 toward a point in the middle between the light-blocking plates 13 so that the central light-blocking plates 16, together with the light-blocking plates 13, define a W-shaped cross-sectional configuration. As shown in FIG. 36 (a fourteenth embodiment of the present invention), the central light-blocking plates 16 may be replaced by a single central light-blocking plate 116 which is a relatively small and thin plate projecting from the connecting plate 14 in parallel to the light-blocking plates 13 so as to lie in the central portion of the illuminating optical path.

The number of light-blocking plates 13 is not necessarily limited to two, but may be three or more. Further, the present invention can be carried out in various other modes.

According to the present invention, when the luminous flux of illuminating light entering the light guide of the endoscope is varied by rotating the light-blocking plates, the change in the ratio of the marginal ray bundle to the central ray bundle of light entering the light guide is kept small over a wide range of the luminous flux variation. Therefore, it is possible to minimize variation in the light-distribution and spectral characteristics of illuminating light emanating from the light guide.

As a result, it is possible to obtain favorable color reproducibility which is only slightly affected by luminous flux control of illuminating light. Moreover, since the present invention has a simplified arrangement, the light source apparatus can be produced at reduced cost.

In addition, according to the present invention, one or more central light-blocking plates block the central portion of the optical path of illuminating light entering the light guide of the endoscope in association with the light-blocking operation of the light-blocking plates for blocking the illuminating optical path. Therefore, even when the light-blocking area is widened, flicker of illuminating light entering the light guide is inconspicuous. Consequently, it is possible to obtain an endoscopic image which is easy to see, and hence possible to make an accurate diagnosis and to give a proper medical treatment. Moreover, the advantageous effect can be extremely easily obtained simply by changing the configuration of the light-blocking plates.

While the invention has been described by reference to specific embodiments chosen for purposes of illustration, it should be apparent that numerous modifications could be made thereto by those skilled in the art without departing from the basic concept and scope of the invention.

We claim:

1. A light source apparatus for an endoscope comprising a light source for emitting a bundle of illuminating light rays to be supplied to a light guide of the endoscope, said light source apparatus comprising:

at least a pair of light-blocking plates disposed in the bundle of illuminating light rays to face each other across an optical axis of the bundle of illuminating light rays;

means for rotatably supporting said light-blocking plates such that said light-blocking plates are rotatable about an axis extending between said light-blocking plates perpendicular to the optical axis of said bundle of illuminating light rays; and at least one of said light-blocking plates comprises a cross-sectional configuration, as viewed in the direction of said optical axis of the bundle of illuminating light rays when said light-blocking plates lie parallel to said optical axis, such that said at least one light-blocking plate is bent at an angle to said axis of rotation at a position near a center of said illuminating optical path, said light blocking plates having a shape such that a ratio between a peripheral portion of the bundle of illuminating light rays and a central portion of the bundle of illuminating light rays is maintained substantially constant as said pair of light blocking plates are rotated by said rotatable supporting means between blocking and nonblocking positions, said central portion of said bundle of illuminating light rays and said peripheral portion of said bundle of illuminating light rays being defined such that when said light blocking plates are in said nonblocking position, the luminous flux of said central portion of the illuminating light rays is equal to the luminous flux of said peripheral portion of the illuminating light rays.

2. A light source apparatus according to claim 1, wherein said light-blocking plates are disposed parallel to and facing each other in the bundle of illuminating light rays across said optical axis of the bundle of illuminating light rays, each said light-blocking plate comprising a crank-shaped cross-sectional configuration, as viewed in the direction of said optical axis of the bundle of illuminating light rays when said light-blocking plates lie parallel to said optical axis.

3. A light source apparatus according to claim 2, wherein said crank-shaped cross-sectional configuration comprises two right angle bends at a position near the center of the bundle of illuminating light rays.

4. A light source apparatus according to claim 3, wherein said light-blocking plates are in bilateral symmetry with respect to said axis of rotation.

5. A light source apparatus according to claim 4, wherein said light-blocking plates are disposed such that a spacing between said light-blocking plates is approximately equal to an effective radius of the bundle of illuminating light rays at a first position, and a spacing between said light-blocking plates is approximately 0.9 times said effective radius at a second position.

6. A light source apparatus according to claim 3, wherein said light-blocking plates comprise crank-shaped cross-sectional configurations in point symmetry with respect to said optical axis of the bundle of illuminating light rays, as viewed in the direction of said optical axis.

7. A light source apparatus according to claim 1, wherein each of said light-blocking plates comprises a a lower portion which lies parallel to said axis of rotation, an intermediate portion which is bent to slightly extend inwardly, and an upper portion which extends upwardly and away from said axis of rotation.

8. A light source apparatus according to claim 1, wherein each of said light-blocking plates comprises a a lower portion which lies parallel to said axis of rotation, an intermediate portion which is bent to slightly extend inwardly, and an upper portion which extends upwardly and away from said axis of rotation, and an other of said light-blocking plates is in point symmetry with said one light-blocking plate with respect to said optical axis of the bundle of illuminating light rays.

9. A light source apparatus according to claim 1, wherein said light-blocking plates are disposed such that upper portions of said light-blocking plates extend upwardly and away from each other, and lower portions of said light-blocking plates extend downwardly and away from each other, so that a spacing between said light-blocking plates is a minimum at an intermediate portion thereof.

10. A light source apparatus according to claim 9, wherein one of said light-blocking plates is a flat plate.

11. A light source apparatus according to claim 1, wherein said light-blocking plates are disposed such that upper portions of said light-blocking plates extend upwardly and toward each other, and lower portions of said light-blocking plates extend downwardly and toward each other, so that a spacing between said light-blocking plates reaches a maximum at an intermediate portion thereof.

12. A light source apparatus according to claim 1, further comprising a third light-blocking plate disposed in the vicinity of said axis of rotation between said light-blocking plates, said third light-blocking plate being shorter in length in the direction of said optical axis than said light-blocking plates.

13. The light source apparatus for an endoscope according to claim 1, said rotatable supporting means comprising means for rotating said light blocking plates between a blocking position in which substantially all of said bundle of illuminating light rays are blocked from reaching said light guide, and a nonblocking position, in which substantially all of said bundle of illuminating light rays are permitted to reach said light guide.

14. A light source apparatus for an endoscope comprising a light source for emitting a bundle of illuminating light rays supplied to a light guide of said endoscope, said light source apparatus further comprising:

at least a pair of light-blocking plates disposed in parallel in the bundle of illuminating light rays to face each other across an optical axis of the bundle of illuminating light rays, said light-blocking plates being plane-parallel plates;

means for rotatably supporting said light-blocking plates such that said light-blocking plates are rotatable about an axis which is parallel to surfaces of said light-blocking plates and perpendicular to said optical axis of the bundle of illuminating light rays; and said light-blocking plates disposed such that respective distances from each said light-blocking plate to said axis of rotation are different, said light blocking plates being spaced from said axis of rotation such that a ratio between a peripheral portion of the bundle of illuminating light rays and a central portion of the bundle of illuminating light rays is maintained substantially constant as said pair of light blocking plates are rotated by said rotatable supporting means between blocking and nonblocking positions, said central portion of said bundle of illuminating light rays and said peripheral portion of said bundle of illuminating light rays being defined such that when said light blocking plates are in said nonblocking position, the luminous flux of said central portion of the illuminating light rays is equal to the luminous flux of said peripheral portion of the illuminating light rays.

15. The light source apparatus for an endoscope according to claim 14, said rotatable supporting means comprising means for rotating said light blocking plates between a blocking position, in which substantially all of said bundle of illuminating light rays are blocked from reaching said light guide and a nonblocking position, in which substantially all of said bundle of illuminating light rays are permitted to reach said light guide.

16. A light source apparatus for an endoscope comprising a light source for emitting a bundle of illuminating light rays supplied to a light guide of said endoscope, said light source apparatus further comprising:

at least a pair of light-blocking plates disposed in parallel in the bundle of illuminating light rays to face each other across an optical axis of the bundle of illuminating light rays, said light-blocking plates being of unequal length in the direction of said optical axis; and means for rotatably supporting said light-blocking plates such that said light-blocking plates are rotatable about an axis which is perpendicular to said axis of the bundle of illuminating light rays and which extends between said light-blocking plates, said light blocking plates having lengths in the direction of the optical axis such that a ratio between a peripheral portion of the bundle illuminating light rays and a central portion of the bundle of illuminating light rays is maintained substantially constant as said pair of light blocking plates are rotated by said rotatable supporting means between blocking and nonblocking positions, said central portion of said bundle of illuminating light rays and said peripheral portion of said bundle of illuminating light rays being defined such that when said light blocking plates are in said nonblocking position, the luminous flux of said central portion of the illuminating light rays is equal to the luminous flux of said peripheral portion of the illuminating light rays.

17. A light source apparatus according to claim 16, wherein said light-blocking plates are plane-parallel plates.

18. The light source apparatus for an endoscope according to claim 16, said rotatable supporting means comprising means for rotating said light blocking plates between a blocking position, in which substantially all of said bundle of illuminating light rays are blocked from reaching said light guide, and a nonblocking position, in which substantially all of said bundle of illuminating light rays are permitted to reach said light guide.

19. A light source apparatus for an endoscope comprising a light source for emitting a bundle of illuminating light rays supplied to a light guide of said endoscope, said light source apparatus further comprising:

at least a pair of light-blocking plates disposed in parallel in the bundle of illuminating light rays to face each other across an optical axis of the bundle of illuminating light rays;

means for rotatably supporting said light-blocking plates such that said light-blocking plates are rotatable about an axis extending between said light-blocking plates perpendicular to said optical axis of the bundle of illuminating light rays; and a central light-blocking plate for blocking a central portion of the bundle of illuminating light rays as the bundle of illuminating light rays is gradually blocked by the rotation of said light-blocking plates, said light blocking plates and said central light blocking plate being configured such that a ratio between a peripheral portion of the bundle of illuminating light rays and a central portion of the bundle of illuminating light rays is maintained substantially constant as said pair of light blocking plates are rotated by said rotatable supporting means between blocking and nonblocking positions, central portion of said bundle of illuminating light rays and said peripheral portion of said bundle of illuminating light rays being defined such that when said light blocking plates are in said nonblocking position, the luminous flux of said central portion of the illuminating light rays is equal to the luminous flux of said peripheral portion of the illuminating light rays.

20. A light source apparatus according to claim 19, wherein said central light-blocking plates comprises a light-blocking plate shorter in length in the direction of said optical axis than said light-blocking plates; said central light-blocking plate extending obliquely from each of said light-blocking plates toward a central portion of the bundle of illuminating light rays.

21. A light source apparatus according to claim 19, wherein said central light-blocking plate is a light-blocking plate shorter in length, in the direction of said optical axis than said light-blocking plates, and is disposed between and parallel to said light-blocking plates.

22. The light source apparatus for an endoscope according to claim 19, said rotatable supporting means comprising means for rotating said light blocking plates between a blocking position in which substantially all of said bundle of illuminating light rays are blocked from reaching said light guide, and a nonblocking position, in which substantially all of said bundle of illuminating light rays are permitted to reach said light guide.

* * * * *

UNITED STATES PATENT AND TRADEMARK OFFICE
CERTIFICATE OF CORRECTION

PATENT NO. : 5,488,509
DATED : January 30, 1996
INVENTOR(S) : T. TAKAHASHI et al.

It is certified that error appears in the above-indentified patent and that said Letters Patent is hereby corrected as shown below:

At column 10, line 60 (claim 7, line 2), delete "a" (second occurrence).

At column 10, line 66 (claim 8, line 2), delete "a" (second occurrence).

At column 12, line 23 (claim 16, line 17), after "bundle" insert ---of---.

Signed and Sealed this

First Day of October, 1996

Attest:

BRUCE LEHMAN

Attesting Officer        Commissioner of Patents and Trademarks